(12) United States Patent
Allard et al.

(10) Patent No.: US 6,660,280 B1
(45) Date of Patent: Dec. 9, 2003

(54) COLLAGEN PRODUCT CONTAINING COLLAGEN OF MARINE ORIGIN WITH A LOW ODOR AND PREFERABLY WITH IMPROVED MECHANICAL PROPERTIES, AND ITS USE IN THE FORM OF COSMETIC OR PHARMACEUTICAL COMPOSITIONS OR PRODUCTS

(75) Inventors: Roland Allard, St. Genis Laval (FR); Nabil Abdul Malak, Caluire (FR); Alain Huc, Ste. Foy les Lyon (FR)

(73) Assignee: Coletica, Lyons (FR)

( * ) Notice: Subject to any disclaimer, the term of this patent is extended or adjusted under 35 U.S.C. 154(b) by 0 days.

(21) Appl. No.: 09/435,934

(22) Filed: Nov. 9, 1999

(30) Foreign Application Priority Data

May 19, 1999 (FR) .............................. 99 06326

(51) Int. Cl.$^7$ .............................. A61K 6/00; A61K 7/00; A61K 9/70; A61K 35/12; A61F 13/00
(52) U.S. Cl. ...................... 424/401; 424/443; 424/520; 424/572; 530/356; 530/856
(58) Field of Search .............................. 530/356, 355, 530/857; 435/240; 160/160.1; 424/443, 401, 526, 572

(56) References Cited

U.S. PATENT DOCUMENTS

| | | | |
|---|---|---|---|
| 5,093,474 A | * 3/1992 | Grossman et al. | 530/355 |
| 5,166,187 A | 11/1992 | Collombel et al. | |
| 5,264,551 A | 11/1993 | Petite et al. | 530/356 |
| 5,273,900 A | 12/1993 | Boyce | 435/240.23 |
| 5,331,092 A | 7/1994 | Huc et al. | 530/356 |
| 5,412,076 A | 5/1995 | Gagnieu | |
| 5,420,248 A | 5/1995 | Devictor et al. | 530/356 |

FOREIGN PATENT DOCUMENTS

| | | |
|---|---|---|
| DE | 226 153 A3 | 8/1995 |
| EP | 0 602 297 A1 | 6/1994 |
| EP | 0 686 402 A1 | 12/1995 |
| EP | 0 753 313 A1 | 1/1997 |
| EP | 0 789 074 A1 | 8/1997 |
| FR | 592.603 | 8/1925 |
| FR | 2 679 778 | 2/1993 |
| FR | 2 724 563 | 3/1996 |
| FR | 2 783 429 | 3/2000 |
| GB | 2 238 051 A | 5/1991 |
| JP | 05049862 | * 3/1993 |
| WO | WO 89/08467 | 9/1989 |
| WO | WO 90/12055 | 10/1990 |
| WO | WO 91/16010 | 10/1991 |
| WO | WO 95/17428 | 6/1995 |
| WO | WO 96/08277 A1 | 3/1996 |
| WO | WO 97/20569 | 6/1997 |
| WO | WO 99/19005 A | 4/1999 |

OTHER PUBLICATIONS

Chemical Abstracts, vol. 112, No. 8, Feb. 19, 1990, abstract No. 58724, "Manufacture of aqueous collagen–containing solutions from fish skin" XP002127982.

D.B. JosephsOn: bisulfite suppression of fish aromas:, Journal of Food Science, vol. 48, 1983, pp. 1064–1067, XP002127981.

Patent Abstracts of Japan, vol. 015, No. 275, Jul. 12, 1991, & JP 03 094633A, Apr. 19, 1991.

France Search Report dated Feb. 2, 2000.

Yeh et al., "A Novel Native Matrix for Tissue Engineering. Analysis of Cell–Matrix Interaction". Faseb Journal, vol. 14, No. 4, Mar. 15, 2000.

Derwent accession No. 1995–151478 & JP 07 075566 A, Marino Forum 21 SH, Mar. 20, 1995.

Wang et al., "Collagen Fibres with Improved Strength for the Repair of Soft Tissue Injuries". Biomaterials, vol. 15, No. 7 (1994): pp. 507–512.

Giraud–Guille et al. "Structural Aspects of Fish Skin Collagen which Forms Ordered Arrays via Liquid Crystalline States". Biomaterials, vol. 21, No. 9 (May 2000): pp. 899–906.

* cited by examiner

Primary Examiner—Sreeni Padmanabhan
Assistant Examiner—Lauren Q. Wells
(74) Attorney, Agent, or Firm—Merchant & Gould, P.C. (23552)

(57) ABSTRACT

The invention relates to a collagen product containing collagen of marine origin with a low odor. The collagen product includes one or more collagens or derivatives thereof, including hydrolyzates, with a low odor, at least part of the collagen or the derivatives being of marine origin and having been subjected to a deodorization treatment, particularly with an oxidizing substance such as a sulfite, hydrogen peroxide or ozone, at any stage of the manufacture of the collagen product. The invention also makes it possible to improve the mechanical properties and to use this low-odor collagen product in cosmetic or pharmaceutical products.

47 Claims, No Drawings

COLLAGEN PRODUCT CONTAINING COLLAGEN OF MARINE ORIGIN WITH A LOW ODOR AND PREFERABLY WITH IMPROVED MECHANICAL PROPERTIES, AND ITS USE IN THE FORM OF COSMETIC OR PHARMACEUTICAL COMPOSITIONS OR PRODUCTS

The present invention relates essentially to a collagen product containing collagen of marine origin with a low odor and preferably with improved mechanical properties, to its use in the form of cosmetic or pharmaceutical compositions or products and to the carrying out of tests in vitro, for example in the context of reconstructed tissues. The invention further relates to a process for the preparation of this collagen product containing collagen of marine origin with a low odor.

In an earlier patent application published under No. WO 93/01241, the present Applicant described the use of the unpigmented skin of fish, particularly flatfish, as a novel industrial source of collagen, the process for its extraction and the collagen and biomaterials obtained by said process.

Unpigmented marine collagen, as obtained by the Applicant's previous invention, made it possible to obtain collagen industrially at an acceptable cost by virtue of the large quantities of skins available in industry, particularly skins originating from flatfish.

However, the present inventors set themselves the new technical problem of the odor generated by collagen derived from fish, in solid form; this problem did not arise within the framework of said earlier patent application insofar as the main application concerned its use as one of the components of cosmetic or pharmaceutical compositions in which the other components, present in very large majority, masked the odor by dilution.

The present inventors also set themselves the new technical problem of the odor normally generated by collagen products containing collagen of marine origin obtained from marine animals such as fish, jellyfish, molluscs and shellfish, irrespective of the form of the collagen, including hydrolyzates thereof. In fact, it has also been possible to observe that not only collagens, irrespective of their forms, whether native or not, in the form of atelocollagen, insoluble collagen, particularly collagen fibers, soluble collagen, particularly acid-soluble collagen, or hydrolyzates thereof, have a troublesome odor.

The present inventors have also been able to observe that, especially in the context of the formation of sponges, membranes or masks of collagen products in which the concentration of collagen(s) or hydrolyzates thereof is relatively high, the odor problem becomes troublesome and severely restricts its use, particularly in the field of cosmetics or pharmaceuticals and especially as a biomaterial for topical application, particularly as a mask.

By way of a new technical problem, the present inventors also set themselves the problem of the insufficiency of the mechanical properties of solid biomaterials prepared from a collagen product of marine origin.

Thus the object of the present invention is to solve both the above-mentioned technical problems individually and preferably simultaneously, and particularly preferably without affecting or degrading the collagen(s), making it possible especially to preserve the native character of this collagen or these collagens.

According to the present invention, a solution to both these problems has unexpectedly been found which also makes it possible to obtain the collagen product with satisfactory mechanical properties, especially by virtue of the fact that, if desired, the invention makes it possible to preserve the native character of the collagen.

Thus, according to a first feature, the present invention provides, by way of a novel product, a collagen product containing collagen of marine origin obtained from marine animals such as fish, jellyfish, molluscs and shellfish, which product comprises one or more collagens or derivatives thereof, including hydrolyzates, with a low odor, at least part of said collagen or said derivatives being of marine origin and having been subjected to a deodorization treatment at any stage of the manufacture of the collagen product.

The expression "collagen product" is understood within the framework of the present invention as meaning any product which contains at least one collagen, and any derived product, including hydrolyzates. "Collagen" is understood as meaning any form of collagen, whether native or not, atelocollagen, insoluble collagen, particularly collagen fibers, soluble collagen, particularly acid-soluble collagen, and any derived product, including hydrolyzates. These hydrolyzates can be obtained chemically or enzymatically in a manner well known to those skilled in the art.

Moreover, the collagen or derivatives thereof can be in totally minor or major proportions, irrespective of its form.

Thus the collagen product according to the invention can comprise from 1 to 100% by weight of collagen(s) and derivatives thereof, including hydrolyzates thereof, preferably from 10 to 100% by weight of these products.

Within the framework of the invention, the above-mentioned deodorization treatment can be carried out initially on the collagen(s), derivatives thereof or hydrolyzates thereof, by themselves or in isolation, or on the final collagen product.

Advantageously this low-odor collagen product is obtained by means of a treatment with at least one active substance having a deodorizing effect.

Said active substance is advantageously an oxidizing substance. As the oxidizing substance it is currently preferable to use at least one sulfite, particularly a metabisulfite, or a salt of said sulfite or metabisulfite, and/or hydrogen peroxide or ozone.

An alkali metal or alkaline earth metal, preferably an alkali metal such as sodium or potassium, may be used in particular as the salt of a sulfite. It is also possible to use a partial salt of a sulfite, like metabisulfite or hydrogensulfite, with an alkali metal or alkaline earth metal as defined above.

The proportion of oxidizing substances, particularly sulfite, varies between very wide limits and will generally be between 0.001% and 20% by weight, advantageously between 0.01% and 10% by weight. A proportion which ensures an industrially effective deodorization treatment may be of the order of about 5% by weight, based on the composition containing the marine collagen to be deodorized.

In one particular embodiment of the invention, this deodorization treatment may be carried out on the collagen-containing parts of marine animals, particularly finely divided fish skins, for example fish skins which have been ground.

In another advantageous embodiment of the invention, the deodorization treatment may be carried out on collagen fibers which have been precipitated from a collagen solution obtained from fish skins in at least a first extraction step, or these two treatments may be combined.

In another advantageous embodiment, the deodorization treatment is carried out on a collagen gel or a solution of collagen hydrolyzate brought into contact with ozone, particularly at an ozone flow rate of between 25 and 50 l/hour per kg of gel, the ozone content being between 20 and 50 mg/l. This deodorization with ozone may be effected by bubbling this gas into the collagen gel or the solution of collagen hydrolyzate.

According to yet another advantageous characteristic of the invention, which is actually preferred, this collagen product has improved mechanical properties and has undergone a crosslinking treatment which initially cannot be a chemical crosslinking; this is because the latter takes place in a liquid or aqueous medium on a solid sponge of very low mechanical strength and generally culminates in a disaggregation of the collagen sponge. Thus, within the framework of the invention, it is preferable to carry out a non-chemical crosslinking, preferably a physical crosslinking and particularly preferably a crosslinking by thermal dehydration, abbreviated to TDH. In this context it is preferable to carry out a thermal dehydration under vacuum at a temperature above 60° C., advantageously of between about 110 and about 130° C. and particularly of the order of 110° C.

After a first non-chemical crosslinking has been carried out, preferably by TDH, it is then possible to strengthen the crosslinking further by performing a chemical crosslinking because, at this point, the mechanical strength of the collagen is sufficiently high to allow a chemical crosslinking. Chemical crosslinking agents are known to those skilled in the art and an example which may be mentioned is the crosslinking with azide described in earlier patent application Ser. No. 5,264,551 in the name of the Applicant.

The source of marine collagen used is preferably fish skins, it being possible to use any fish skins in this context. Advantageously, however, it is preferable to use a fish skin which is collected industrially because it is generally cut away from the fresh fish directly at the fishing site and is advantageously frozen immediately after removal.

It is generally flatfish which are subjected to a skinning step to extract the fillets, so the skins of flatfish are a practical source of fish skins.

For certain applications it may be advantageous to obtain unpigmented collagen in the manner described in previous patent application WO 93/01241 or U.S. Pat. No. 5,420,248 in the name of the Applicant, so an unpigmented fish skin may be used in certain types of application as the source for preparing the collagen.

Similarly it is also possible to prepare collagen films by drying a collagen gel in a stream of gas, particularly in air, and optionally subjecting it to a physical crosslinking step, particularly by thermal dehydration, which can be followed by a chemical crosslinking step.

According to a second feature, the present invention also covers a sponge, membrane or mask comprising marine collagen preferably obtained from fish skins, wherein the collagen has been subjected to a deodorization treatment, advantageously as defined above, during its manufacturing process. According to an advantageous characteristic, the sponge, membrane or mask comprises marine collagen which has also been subjected to at least one physical crosslinking as described above, particularly a crosslinking by TDH, by itself or in combination with a subsequent chemical crosslinking, in order to improve its mechanical properties.

According to a third feature, the invention further relates to a process for the manufacture of a collagen product containing collagen of marine origin, which comprises carrying out a deodorization treatment on the collagen itself or on the collagen product, this deodorization treatment preferably being carried out with at least one active substance having a deodorizing effect.

Other advantageous characteristics of the treatment process are clearly apparent to those skilled in the art from the above description relating to the collagen product itself, and from the Examples below, which are given simply by way of illustration but form an integral part of the invention. In the Examples, any characteristic which appears to be novel compared with any state of the art forms an integral part of the present invention in most instances. In addition, all the percentages are given by weight, unless indicated otherwise.

Within the framework of the invention, the collagen product can contain collagen which has been subjected to a deodorization treatment, optionally mixed with untreated collagen or collagen from a source other than a marine source.

Furthermore, among marine animals, fish are currently the preferred source of collagen of marine origin, particularly fish skins.

According to a fourth feature, the invention further relates to cosmetic or pharmaceutical products, especially biomaterials, which are partially or totally produced from the marine collagen product with a low odor and preferably with improved mechanical properties, and especially to sponges, membranes or masks of a marine collagen product, as defined above.

As far as cosmetic products are concerned, the invention is particularly advantageous in the context of collagen-based cosmetic masks. In fact, those skilled in the art are well aware that collagen derived from mammals is to be avoided insofar as this collagen might carry a risk of contamination, and also for ecological reasons. In addition, for reasons of image, the majority of cosmetics companies are increasingly using fewer ingredients originating from mammals. Marine collagen, on the other hand, has so far been unable to find an application because of its strong and unpleasant odor and its low mechanical strength.

The invention therefore makes it possible to provide a satisfactory solution to these two problems which the present inventors were the first to set themselves. In the case of the invention, insofar as it is desirable or necessary for the collagen to have very good mechanical properties, the totally native character of the collagen is very important. A collagen of native character is understood as meaning a collagen which has preserved its helical structure as well as its telopeptides, which carry a large or even major proportion of the collagen's crosslinkages.

Within the framework of the invention, at least one or more cosmetic or pharmaceutical active principles may be incorporated into or added to the collagen, depending on the envisaged application of the collagen, as can easily be understood by those skilled in the art.

By virtue of the invention, it is now possible to use marine collagen in cosmetic or pharmaceutical products, particularly in biomaterials and especially masks, which consist of very thin collagen sponges a few millimeters thick, intended for application to the skin and more particularly to the face. The purpose of these masks is to smooth and whiten the skin. They also give a substantial sensation of well-being. They can serve as a carrier for active ingredients, which will then be released gradually onto the surface of the skin. In this case the active substance can either be introduced into the whole volume of the sponge during manufacture or be applied to the surface of the mask when the latter is in contact with the skin.

In the pharmaceutical field, collagen can be used in the form of sponges in numerous applications: hemostatic sponges, healing dressings and cell culture supports intended for the engineering of tissues, especially reconstructed skin and cartilage. For these applications it is highly desirable to use a collagen which does not originate from a mammal; the present invention makes it possible to meet this requirement.

It should be noted that fish skin is a preferred raw material. It actually has several merits: firstly, it is available in large quantities, particularly in the case of fish consumed as fillets, making it relatively inexpensive; secondly, it is removed industrially under conditions of high cleanliness; finally, it is frozen very rapidly after removal, ensuring that the collagen preserves its native character. The native character is also preserved by the process according to the present invention.

Other characteristics and advantages of the invention will become clearly apparent from the following explanatory description referring to the Examples, which are given simply by way of illustration and cannot in any way limit the scope of the invention.

EXAMPLE 1

Preparation of Low-odor Marine Collagen Using Metabisulfite

1—Preparation of Finely Divided Fish Skins

Complete sole skins, i.e. those containing pigmented and unpigmented skins, are ground while still frozen. Grinding is continued until a finely divided skin is obtained, the resulting fragments having a size of the order of 5 mm. The ground material obtained is washed twice in a phosphate buffer of the following formulation: $Na_2HPO_4(12H_2O)$: 21.7 g/l, $KH_2PO_4$: 0.78 g/l in sterile softened water, the pH being of the order of 7.6–7.8.

The ratio of ground material to buffer is 1 kg/4 l, giving a final volume of 5 l. The two washes each take 1 h at a temperature of 8° C., the ground material being recovered by centrifugation after each wash. The ground material is then rinsed twice in succession with sterile softened water at 8° C., the times, ratio and recovery being the same as for the washing.

The following deodorization treatment can be carried out directly on the ground material washed in this way.

2—Deodorization Treatment

The washed ground material obtained in step 1 above is dispersed in a bath of deodorizing substances, which in this case is sodium metabisulfite at a final concentration of 5% by weight in sterile softened water. The amounts used are of the order of 1 kg of washed ground material to 4 l of bath, the final volume being 5 l. The dispersion is prepared at 8° C. over 2 h and is then left to stand for 72 h, still at 8° C.

3—Rinsing of the Treated Ground Material

After the deodorization treatment, the ground material is recovered by centrifugation and then rinsed with sterile softened water. The weight/volume ratio is 1 kg to 10 l. This operation is repeated three times, still at 8° C. Each of the rinses takes 1 h.

4—Extraction of the Low-odor Marine Collagen

The rinsed ground material obtained in step 3 above is dialyzed against a 0.1 M acetic acid bath in cellulose tubes for 7 days at 8° C. The dialysis bath is renewed every 24 h for 5 days in succession.

The concentration of the last acetic acid bath is increased to 0.25 M and the dialysis time to 48 h. The ground material is subsequently homogenized by ultrasound and then centrifuged at 4000 rpm for 15 min at 8° C. to remove the impurities.

The supernatant is dialyzed against sterile softened water for 72 h, still at 8° C.

The concentration of the collagen gel obtained from the ground material by this extraction operation is of the order of 1.3–1.5% by weight of collagen.

The collagen gel obtained by this process is in the native state, i.e. with its telopeptides and its triple helix structure.

This collagen gel can then be treated in order to prepare sponges, films or masks, as shown in Examples 6 to 8 below, or any other form of solid biomaterial intended for cosmetic or pharmaceutical applications.

EXAMPLE 2

Preparation of Low-odor Marine Collagen Using Ozone

1—Preparation of Finely Divided Fish Skins

The sole skins are prepared and the ground material obtained by the same process as in Example 1.

2—Preparation of the Collagen Gel

The ground material obtained above is placed for 24 hours in a bath of 0.25 M acetic acid solution at a rate of 1 kg to 4 l of solution, the final volume being 5 l.

The mixture obtained is then homogenized by ultrasound using an ULTRATURRAX apparatus. The homogenized material is centrifuged at 400 rpm for 15 min at 8° C. in order to remove the impurities. Only the supernatant is retained.

The concentration of the collagen gel obtained by this operation is of the order of 1.3 to 1.5% by weight of collagen.

3—Deodorization Treatment With Ozone

The collagen gel prepared by the process described in step 2 is deodorized with a stream of ozone.

This is done by placing the gel in a closed reactor inside which a stream of ozone circulates, the ozone being fed in through the bottom of the reactor via a lower inlet provided for this purpose, passing through the gel from bottom to top and leaving through the top of the reactor via an upper outlet provided for this purpose. A commercially available, perforated agitator is provided which is capable of agitating the gel with a chopping effect. It is seen that the ozone passes through the collagen gel, maintained under constant agitation.

The duration of the ozone treatment can vary between 1 h and 10 h. For a weight of treated gel of 1 kg, the ozone flow rate is between 25 and 50 l/hour, the ozone content being between 20 and 50 mg/l and preferably 35 mg/l. The gas is produced by a model Labo 76 <<TRAILIGAZ>>apparatus.

The gel treated with ozone in this way can be used to produce films, collagen sponges, masks or any other form of solid biomaterial intended for cosmetic or pharmaceutical applications, as described in Examples 6 to 8.

EXAMPLE 3

Preparation of Low-odor Marine Atelocollagen Using Ozone

1—Preparation of Finely Divided Fish Skins

The sole skins are prepared and the ground material obtained by the same process as in Examples 1 and 2.

2—Extraction and Preparation of Decrosslinked Marine Collagen With Helical Structure Preserved The ground material obtained is treated by techniques known to those skilled in the art, either with pepsin or with sodium hydroxide solution, to give a partially decrosslinked collagen often referred to as atelocollagen.

After the ground material has been washed, the collagen gel is obtained by the same process as in Example 2.

3—Deodorization Treatment With Ozone

This is carried out by the same technique as in Example 2.

The gel treated in this way can be used to obtain films, collagen sponges or any other form of solid biomaterial intended for cosmetic or pharmaceutical applications.

EXAMPLE 4

Preparation of Low-odor Acid-soluble Marine Collagen Using Ozone

Solutions of acid-soluble marine collagen prepared by techniques known to those skilled in the art can be deodorized with a stream of ozone by the process described in Example 2.

EXAMPLE 5

Preparation of Low-odor Marine Collagen Hydrolyzates Using Ozone

Solutions of marine collagen hydrolyzates obtained by the hydrolysis of fish skins using an enzymatic or chemical technique by processes known to those skilled in the art can be deodorized with a stream of ozone by the process described in Example 2.

EXAMPLE 6

Preparation of a Collagen Sponge

The collagen gel as obtained in Example 1, 2 or 3 can be cast into trays to a desired thickness and then frozen and lyophilized to give collagen sponges.

The mechanical strength of these sponges can be improved by nonchemical crosslinking, advantageously by physical crosslinking and preferably by thermal dehydration. In the context of the present Example, thermal dehydration can consist in heating the collagen sponge at a temperature of about 106° C. for 7 h under a reduced pressure below about 100 Pa, in particular of about 50 Pa (about 500 μbar).

This collagen sponge can be prepared in thicknesses ranging from 0.2 to 2 cm.

The physical crosslinking can optionally be followed by a chemical crosslinking, for example using the azide method.

The sponges obtained from the gels prepared by the techniques described in Examples 1, 2 and 3 have greatly reduced odor levels compared with the sponges obtained without an oxidizing treatment, the most effective deodorization being achieved with ozone.

Furthermore, the latter deodorization technique very substantially improves the mechanical properties of the moist sponges compared with the same biomaterials obtained in conventional manner, even before the physical or chemical crosslinking treatments.

It should also be noted that the sponges prepared with the gel treated with ozone under the conditions described in Example 2 have increased thermal stabilities.

In fact, the denaturation peaks of the collagen of the same sponges, obtained using a SETARAM apparatus, show that if the temperature at the start of denaturation remains unchanged, the temperature at the top of the peak is increased by about 3° C. and the temperature at the end of denaturation is increased by about 14° C.

This result demonstrates that the ozone treatment causes a crosslinking of the collagen under the conditions described in Example 2.

EXAMPLE 7

Preparation of a Collagen Membrane or Film

The collagen gel as obtained in Examples 1, 2 and 3 can be prepared in the form of a collagen membrane or film by being cast onto a tray in a layer of the desired thickness and then dried in air or in a gaseous fluid such as air or nitrogen. As in the case of the sponge, the mechanical properties can be enhanced by thermal dehydration, optionally followed by a chemical crosslinking.

This collagen membrane or film can be obtained in various thicknesses from about 10 to 100 μm, according to the application envisaged. Examples of valuable applications of this biomaterial are the covering of burns or wounds or the stabilization of enzymes by grafting them to the surface of the film.

As with the sponges, the fish odor has been very largely removed from the films obtained after the deodorization treatments described in Examples 1, 2 and 3, the most effective treatment being the ozone technique, and this is the case even before the physical or chemical crosslinking treatments.

For this form of biomaterial, as in the case of the sponges, the mechanical properties of the moist films are greatly improved by the ozone treatment.

EXAMPLE 8

Preparation of a Collagen Mask From Collagen Sponges

The collagen sponges as obtained in Example 2, crosslinked or not by thermal dehydration but not chemically crosslinked, which are also called collagen plaques, can be split to give veils with a thickness of 3 to 4 mm.

After being cut to A4 dimensions, each veil can be compacted at a pressure of 150 kg/cm$^2$, or 150×10$^5$ MPa, to give a thickness of 0.2 mm after compaction.

Each veil can then be cut to the dimensions appropriate for each application (contour of the eyes, lips, bust).

This provides a product constituting a mask, which can be placed in blister packs and then sterilized by any sterilization means well known to those skilled in the art, for example by irradiation with 15 kgray of β rays.

What is claimed is:

1. A collagen product comprising a collagen compound derived from marine animals, wherein said collagen compound has been subjected while present in an aqueous solution to a deodorization treatment with an oxidizing substance consisting essentially of an effective amount of ozone in said aqueous solution.

2. The collagen product of claim 1, wherein sad collagen compound is derived from a marine animal selected from fish, jellyfish, mollusk or shellfish.

3. The collagen product of claim 1, wherein said collagen compound is a collagen hydrolysate.

4. The collagen product of claim 1 which comprises from 1 to 100% by weight of collagen compound.

5. The collagen product of claim 1 which comprises from 10 to 100% by weight of collagen compound.

6. The collagen product of claim 1, wherein said deodorization treatment is carried out before said collagen compound is formed into said collagen product.

7. The collagen product of claim 1, wherein said deodorization treatment is carried out on finely divided fish skins.

8. The collagen product of claim 7, wherein said finely divided fish skins have been ground.

9. The collagen product of claim 1, wherein the deodorization treatment is carried out on collagen fibers which have been precipitated from a collagen solution derived from fish skins, in at least a first extraction step.

10. The collagen product of claim 1 wherein the deodorization treatment is carried out on a collagen gel or a solution of collagen hydrolyzate brought into contact with ozone.

11. The collagen product of claim 1 wherein the deodorization treatment is carried out on a collagen gel or a solution of collagen hydrolyzate brought into contact with ozone at an ozone flow rate in the range of 25 to 50 l/hour per kg of gel, the ozone content being in the range of 20 to 50 mg/l.

12. The collagen product of claim 1 wherein the collagen product has improved mechanical properties by having been subjected to a physical crosslinking.

13. The collagen product of claim 1 wherein the collagen product has improved mechanical properties by having been subjected to a crosslinking by thermal dehydration.

14. The collagen product of claim 13 wherein said thermal dehydration is carried out under vacuum at a temperature above 60° C.

15. The collagen product of claim 13 wherein said thermal dehydration is carried out under vacuum at a temperature in the range of about 100 to about 130° C.

16. The collagen product of claim 13 wherein the pressure of thermal crosslinking is below about 100 Pa.

17. The collagen product of claim 13 wherein the pressure of thermal crosslinking is below or equal to about 50 Pa.

18. The collagen product of claim 1 wherein, after a first non-chemical crosslinking has been carried out, the crosslinking is further strengthened by performing a chemical crosslinking.

19. The collagen product of claim 1 wherein, after a first non-chemical crosslinking has been carried out by thermal dehydration, the crosslinking is further strengthened by performing a chemical crosslinking.

20. The collagen product of claim 18 wherein the chemical crosslinking is carried out with azide.

21. The collagen product of claim 1, wherein the collagen compound is derived from a fish skin which is collected industrially.

22. The collagen product of claim 21, wherein said industrial collection of fish skin comprises cutting the skin away from the fresh fish directly at the fishing site.

23. The collagen product of claim 1 wherein the collagen compound is obtained from a fish skin which is collected industrially by cutting it away from the fresh fish directly at the fishing site and is frozen immediately after removal.

24. The collagen product of claim 1 wherein the collagen compound is obtained from the skin of flatfish subjected to a skinning step to extract the fillets.

25. The collagen product of claim 1, wherein the collagen compound is derived from an unpigmented fish skin.

26. The collagen product of claim 1, wherein the collagen product is in a form selected from the group consisting of: a collagen film, a collagen membrane, a cosmetic collagen mask, and a collagen sponge.

27. The collagen product of claim 26, wherein said collagen product is prepared in the form of a collagen film dried in a stream of air.

28. The collagen product of claim 26, wherein said collagen product is prepared in the form of a collagen film dried by lyophilization.

29. The collagen product of claim 1, wherein said deodorization treatment also improves the mechanical properties of said collagen product.

30. The collagen product of claim 1, wherein said deodorization treatment also improves the thermal stability of said collagen product.

31. A collagen product comprising a collagen compound obtained from at least one marine animal, wherein said collagen compound has been subjected to a deodorization treatment with an oxidizing substance consisting essentially of ozone in aqueous solution at a flow rate of between about 25 and 50 l/hour/kg of collagen compound, wherein said ozone concentration is between about 20 and 50 mg/l.

32. A method of making hemostatic sponges, healing dressings, or cell culture supports comprising utilizing the collagen product of claim 1.

33. The collagen product of claim 32, wherein said cell culture supports can be used for engineering tissues, reconstructing skin, reconstructing cartilage, and combinations thereof.

34. A sponge, membrane or mask comprising a marine collagen compound, wherein the collagen compound has been subjected to a deodorization treatment while present in an aqueous solution with an oxidizing substance consisting essentially of an effective amount of ozone in said aqueous solution.

35. The sponge, membrane or cosmetic mask comprising a marine collagen compound of claim 34, wherein said collagen compound is a collagen hydrolysate.

36. The sponge, membrane or mask comprising a marine collagen compound of claim 35, wherein the collagen compound is derived from fish skins.

37. The sponge, membrane or mask comprising a marine collagen compound of claim 34, wherein the collagen compound is derived from a marine animal selected from the group of fish, jelly fish, and shell fish.

38. The sponge, membrane or cosmetic mask of claim 34, wherein said deodorization treatment with ozone is carried out on a collagen gel or a solution of collagen hydrolyzate brought into contact with ozone at an ozone flow rate in the range of 25 to 50 l/hour per kg of gel, the ozone content being in the range of 20 to 50 mg/l.

39. A cosmetic or pharmaceutical product comprising a collagen product comprising a collagen compound derived from marine animals, wherein said collagen compound has been subjected while present in an aqueous solution to a deodorization treatment with an oxidizing substance consisting essentially of an effective amount of ozone in said aqueous solution; and a cosmetically or pharmaceutically acceptable excipient.

40. The cosmetic or pharmaceutical product of claim 39, which is a biomaterial.

41. The cosmetic or pharmaceutical product of claim 39, wherein the collagen compound has been submitted to a crosslinking to improve mechanical properties thereof.

42. The cosmetic or pharmaceutical product of claim 39, wherein said collagen product is derived from a marine animal selected from the group consisting of fish, jelly fish, mollusk and shell fish.

43. The cosmetic of pharmaceutical product of claim 39, wherein the deodorization treatment with ozone is carried out on a collagen gel or a solution of collagen hydrolyzate brought into contact with ozone at an ozone flow rate in the range of 25 to 50 l/hour per kg of gel, the ozone content being in the range of 20 to 50 mg/l.

44. A process for the manufacture of a collagen product according to claim 1 comprising carrying out a deodorization treatment on the marine collagen compound or on the collagen product, while present in an aqueous solution, with an oxidizing substance consisting essentially of an effective amount of ozone in said aqueous solution.

45. The process of claim 44, wherein said collagen compound is derived from a marine animal selected from the group consisting of fish, jelly fish, mollusk and shell fish.

46. The process of claim 44, which comprises carrying out a deodorization treatment on the marine collagen compound on a collagen gel brought into contact with ozone at an ozone flow rate in the range of 25 to 50 l/hour per kg of gel, the ozone content being in the range of 20 to 50 mg/l.

47. The process of claim 44, which comprises carrying out the ozone deodorization treatment on the collagen product.

* * * * *